United States Patent
Jasperse et al.

(10) Patent No.: US 10,772,573 B2
(45) Date of Patent: Sep. 15, 2020

(54) APPARATUS, SYSTEM AND METHOD FOR ASSISTING IN PROVIDING A DIAGNOSIS OF A MEDICAL CONDITION OF A MAMMAL BRAIN AS WELL A COMPUTER READABLE MEDIUM COMPRISING A PROGRAM FOR CARRYING OUT THE METHOD

(71) Applicant: Erasmus University Medical Center Rotterdam, Rotterdam (NL)

(72) Inventors: Bas Jasperse, Rotterdam (NL); Marcel Koek, Rotterdam (NL); Gabriel Krestin, Rotterdam (NL); Wiro Niessen, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 430 days.

(21) Appl. No.: 15/743,209

(22) PCT Filed: Jul. 8, 2016

(86) PCT No.: PCT/NL2016/050499
§ 371 (c)(1),
(2) Date: Jan. 9, 2018

(87) PCT Pub. No.: WO2017/010873
PCT Pub. Date: Jan. 19, 2017

(65) Prior Publication Data
US 2018/0206800 A1    Jul. 26, 2018

Related U.S. Application Data

(63) Continuation of application No. PCT/NL2015/050505, filed on Jul. 10, 2015.

(51) Int. Cl.
*A61B 5/00*     (2006.01)
*G06T 7/00*     (2017.01)
(Continued)

(52) U.S. Cl.
CPC .......... *A61B 5/7435* (2013.01); *A61B 5/0042* (2013.01); *A61B 5/055* (2013.01);
(Continued)

(58) Field of Classification Search
CPC ..... A61B 5/0042; A61B 5/055; A61B 5/7435; A61B 6/032; A61B 6/463; A61B 6/465;
(Continued)

(56) References Cited

U.S. PATENT DOCUMENTS

| 2010/0021035 A1* | 1/2010 | Gupta | G06T 7/68 |
| | | | 382/131 |
| 2013/0243291 A1* | 9/2013 | Varsha | A61B 6/03 |
| | | | 382/131 |

FOREIGN PATENT DOCUMENTS

WO    2011142725 A1    11/2011

OTHER PUBLICATIONS

International Search Report and Written Opinion dated Oct. 12, 2016 in PCT Application No. PCT/NL2016/050499.
(Continued)

*Primary Examiner* — Michael T Rozanski
(74) *Attorney, Agent, or Firm* — McDermott Will & Emery LLP

(57) ABSTRACT

An apparatus is disclosed for assisting in providing a diagnosis of a medical condition of a mammal brain. The apparatus includes an input facility, a conversion facility, and an output device. In an operational mode the input facility receives a first value and a second value. The input facility further receives first reference data indicative for a cumulative distribution of the first value for said portion in a reference population and second reference data indicative for a cumulative, distribution of the second value for the corresponding portion in the reference, population. The conversion facility determines a third value indicating the
(Continued)

cumulative probability of the first value and a fourth value indicating the cumulative probability of the second value. The output device generates a signal indicating a substantially monotonically increasing function of a difference between the third and the fourth value.

14 Claims, 10 Drawing Sheets

(51) Int. Cl.
    *G06T 7/68*     (2017.01)
    *A61B 5/055*     (2006.01)
    *A61B 6/03*     (2006.01)
    *A61B 6/00*     (2006.01)
    *G06T 11/20*     (2006.01)

(52) U.S. Cl.
    CPC .............. *A61B 6/032* (2013.01); *A61B 6/463* (2013.01); *A61B 6/465* (2013.01); *G06T 7/0012* (2013.01); *G06T 7/0014* (2013.01); *G06T 7/68* (2017.01); *G06T 11/206* (2013.01); *G06T 2207/10081* (2013.01); *G06T 2207/10088* (2013.01); *G06T 2207/20076* (2013.01); *G06T 2207/20081* (2013.01); *G06T 2207/30016* (2013.01)

(58) Field of Classification Search
    CPC ......... G06T 11/206; G06T 2207/10081; G06T 2207/10088; G06T 2207/20076; G06T 2207/20081; G06T 2207/30016; G06T 7/0012; G06T 7/0014; G06T 7/68
    See application file for complete search history.

(56) References Cited

OTHER PUBLICATIONS

Yoon, Uicheul, et al. "Quantitative analysis of group-specific brain tissue probability map for schizophrenic patients", NeuroImage, vol. 26, No. 2, pp. 502-512, Jun. 1, 2005.

* cited by examiner

APPARATUS, SYSTEM AND METHOD FOR ASSISTING IN PROVIDING A DIAGNOSIS OF A MEDICAL CONDITION OF A MAMMAL BRAIN AS WELL A COMPUTER READABLE MEDIUM COMPRISING A PROGRAM FOR CARRYING OUT THE METHOD

RELATED APPLICATIONS

This application is a United States National Phase under 35 U.S.C. § 371 of International Application No. PCT/NL2016/050499, filed on Jul. 8, 2016, which claims the benefit of, and priority to, International Patent Application No. PCT/NL2015/050505, filed on Jul. 10, 2015, both of which are hereby incorporated by reference in their entirety for all purposes.

BACKGROUND

WO2008069762 discloses a method for identifying a pathological region within a scan. The scan may be of any kind in which there is difference of intensity between normal and pathological regions. It particularly relates to a method for identifying brain scan slices that may include an acute ischemic stroke region, a method for distinguishing a brain hemisphere having the stroke region, and systems and software for performing the methods. The method analyses the intensity distribution of pixel values obtained as a result from the scan by a procedure including the following steps.

First the intensity distribution of each slice is determined, therewith obtaining a histogram specifying the frequency with which a certain pixel intensity occurs. Next percentile values are determined, i.e. indicating the pixel intensity below which a given percentage of all measured pixel intensities fall in the obtained histogram. A single parameter R is extracted from these percentile values by the following expression:

$$R = P_{50}\left[\frac{P_{b+20} - P_b}{P_{d+20} - P_d}\right]$$

Therein $P_x$ indicates a percentile for a percentage x, and further b>50 and d<50. The value $P_{b+20}-P_b$ is denoted the "bright band difference", referring to the intensity difference between the top and bottom end of the "bright band" of the histogram and the value $P_{d+20}-P_d$ is denoted the "dark band difference" referring to the intensity difference between the top and bottom end of the "dark band" of the histogram. Subsequently the difference obtained between the value of the parameter for the left hemisphere and the right hemisphere in a same slice are used as an indication of the presence of a pathological condition.

Whereas the known method may provide acceptable results for the type of pathological condition as considered in the above-cited WO2008069762, other pathological conditions may be less clearly visible, such as in early stages of dementia.

It is noted that WO 2011/142725 A1 discloses the analysis of brain functionality by comparing intensity distributions between brain hemispheres. Apart from intensity distributions, other characteristics include numerical parameters indicative of the characteristics of a body region such as percentiles and percentile ratios indicative for said intensity distributions.

It is further noted that Yoon et al. in "Quantitative analysis of groups-specific brain tissue probability map for schizophrenic patients", discloses group-specific brain tissue probability maps derived from healthy control subjects and schizophrenic patients. This article is published in NeurolImage 26 (2005), pp 502-512.

SUMMARY

It is an object of the present invention to provide an improved apparatus for assisting a medical professional in providing a diagnosis of a medical condition of a mammal brain.

It is a further object of the present invention to provide an improved system including the improved apparatus for assisting a medical professional in providing a diagnosis of a medical condition of a mammal brain.

It is a still further object of the present invention to provide an improved method for assisting a medical professional in providing a diagnosis of a medical condition of a mammal brain.

It is a still further object of the present invention to provided a computer accessible medium comprising a computer program with instructions for causing a programmable computer to execute each of the steps of the improved method.

In accordance with the first-mentioned object, as a first embodiment an apparatus is provided for assisting in providing a diagnosis of a medical condition of a mammal brain, the brain having a first and a second part. The apparatus includes an input facility, a conversion facility, and an output device. The apparatus is configured and arranged such that in an operational mode of the apparatus the input facility receives at least one pair of values and at least one pair of reference values.

The at least one pair of values includes:
  a first value indicative of a brain characteristic of a portion of the first part of the brain for a point in time;
  a second value indicative of a medical brain characteristic of a corresponding portion of the second part of the brain for said point in time.

The at least one pair of reference values includes:
  first reference data indicative for a cumulative distribution of said first value for said portion in a reference population; and
  second reference data indicative for a cumulative distribution of said second value for said corresponding portion in said reference population.

The conversion facility determines a third value, indicating the cumulative probability of said first value according to said first reference data and a fourth value, indicating the cumulative probability of said second value according to said second reference data. The output device generates a human accessible output signal which is indicative for a substantially monotonically increasing function of a difference between the third and the fourth value.

The inventors recognized that the human accessible output signal as generated by the apparatus as provided herewith enables the medical professional to earlier recognize a medical disorder of the brain with more confidence.

The apparatus may be provided as a separate device. The separate device may receive the first value and the second value, as well as the first and second reference data from another location, e.g. by an internet connection.

Alternatively, the separate device may be coupled with a scanning device, such as an MRI scanner arranged in the neighborhood of the separate device that is equipped with image analysis means to provide the first value and the second value of the at least one pair of values by analysis of image data obtained with the scanning device. Such a scanning device with image analysis means may also have been used to gather the first and second reference data and have a storage space for storing this reference data to be provided to the separate device.

Alternatively, storage space for storing reference data may be provided at a remote location, and the reference data may (also) be provided by image analysis of image data obtained from other scanning devices, such as a CT-scanner.

In accordance with the above-mentioned objects, as a second embodiment a system is provided that comprises an apparatus according to the first embodiment and that further comprises one or more of a scanning device with image analysis functionality for determining the first value and the second value; and a storage facility for storing and providing said first and said second reference data.

In accordance with the above-mentioned objects, as a third embodiment a method is provided for assisting a medical professional in providing a diagnosis of a medical condition of a mammal brain, the brain having a first and a second part.

The method according to this third embodiment includes:
receiving at least one pair of values and at least one pair of reference values.

The at least one pair of values includes:
a first value indicative of a brain characteristic of a portion of the first part of the brain for a point in time;
a second value indicative of a brain characteristic of a corresponding portion of the second part of the brain for said point in time.

The at least one pair of reference values includes:
first reference data indicative for a cumulative distribution of said first value for said portion in a reference population; and
second reference data indicative for a cumulative distribution of said second value for said corresponding portion in said reference population.

Having received the at least one pair of values and the at least one pair of reference values, the method proceeds by:
determining a third value, indicating the cumulative probability of said first value according to said first reference data and a fourth value, indicating the cumulative probability of said second value according to said second reference data, and
generating a human accessible output signal which is indicative for a substantially monotonically increasing function of a difference between the third and the fourth value.

In accordance with the above-mentioned objects, as a fourth embodiment a computer accessible medium comprising a computer program with instructions for causing a programmable computer is provided to execute each of the steps of the method according to the third embodiment.

In an embodiment, the first and the second part are the left and the right hemisphere of the brain. Nevertheless the parts from which the portions to be compared are selected may also be other parts. Also the comparison may involve a combination of mutually corresponding portions from the left and the right hemisphere of the brain and a mutually corresponding portions from a pair of otherwise defined parts of the brain.

The inventive apparatus and method facilitates a medical specialist in establishing a diagnosis of a subject. For example, Alzheimer disease (AD) tends to a generally symmetric atrophy in multiple parts of the brain, in particular the temporal, parietal and hippocampi areas. Atrophy of the frontal and temporal regions in case of fronto-temporal dementia (FTD) often occurs asymmetrically. Also Cortico-basal Degeneration tends to occur in an asymmetric manner. On the other hand Lewy Body dementia typically is visible as a substantially symmetric atrophy.

BRIEF DESCRIPTION OF THE DRAWINGS

These and other aspect are described in more detail with reference to the drawings. Mutually corresponding parts are indicated therein with the same reference.

In the drawings.

DETAILED DESCRIPTION OF EMBODIMENTS

Figure 1:
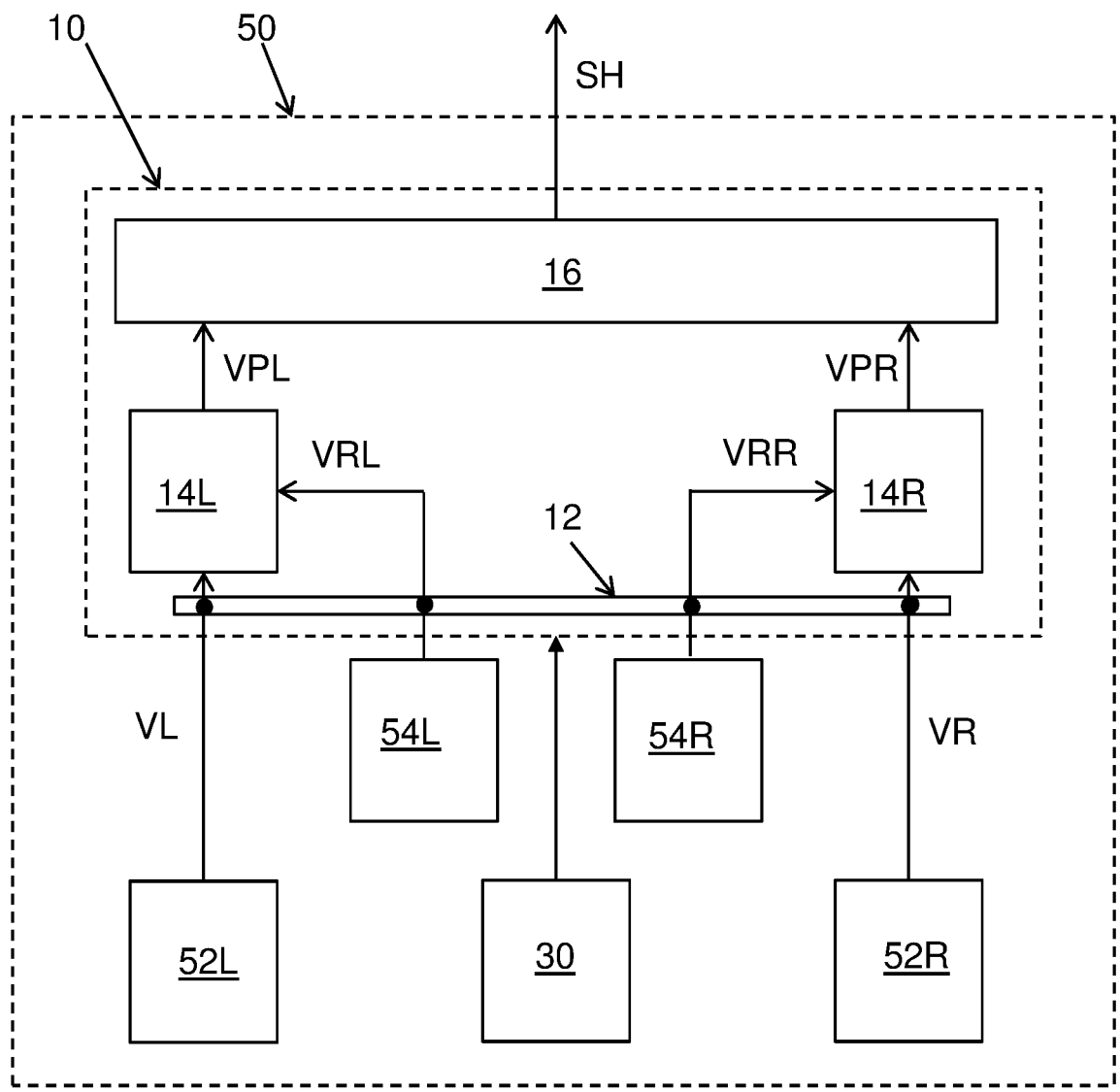
FIG. 1 schematically shows an apparatus for assisting in providing a diagnosis of a brain characteristic of a mammal brain, FIG. 2 schematically shows a method for assisting in providing a diagnosis of a medical condition of a mammal brain.

FIG. 1 schematically shows an apparatus 10 for assisting in providing a diagnosis of a brain characteristic of a mammal brain. The apparatus 10 includes an input facility 12, a conversion facility 14L, 14R, and an output device 16. The apparatus is configured and arranged such that in an operational mode of the apparatus the input facility 12 receives a pair of values VL, VR and a pair of reference values VRL, VRR. The pair of values includes a first value VL indicative of a brain characteristic of a portion of a first part of the brain, here the left hemisphere (also denoted as left part) for a point in time and a second value VR indicative of a brain characteristic of a corresponding portion of a second part of the brain, here the right hemisphere (also denoted as right part) for that point in time.

In this connection it is noted that a portion of the left part of the brain may comprise one of the left frontal lobe, left parietal lobe, left occipital lobe, left temporal lobe, left limbic lobe, and left hippocampus. Still further more specific neuroanatomical regions can be identified in the brain. For example the cortex can be sub-divided into 49 "parcellation units" (PUs), which are mutually bounded by a sulcus, i.e. a depression or fissure between the folds of cortical grey matter (gyri). A corresponding portion of the right part of the brain is that part which is symmetrically arranged with respect to the portion of the left part of the brain that is considered. E.g. the corresponding portion of the left frontal lobe is the right frontal lobe.

A brain characteristic may be any feature which can describe (phenotype) the brain. Examples are

- brain morphology [1,2,5,6,7]. This may include characteristics for volume and shape description of brain tissues, brain lobes and individual neurostructures (e.g. hippocampus)
- brain function [11]. This includes for example resting state fMRI measurements, functional MR measurements, and brain perfusion, e.g. as determined by arterial spin labeling (ASL)),
- brain connectivity [8,9,10]. Characteristics indicative for brain connectivity are for example diffusion measures such as fractional anisotropy and mean diffusivity, per region or tract, and
- brain pathology [3,4]. Examples are white matter integrity, e.g. in terms of white matter lesions, microbleeds, enlarged Virchow and Robin spaces etc. in certain regions.

Literature further discussing these characteristics and corresponding measurement methods is specified by the bracketed number in the list of references attached herewith.

The pair of reference values includes first and second reference data. The first reference data VRL indicates a cumulative distribution of the first value for the portion, e.g. for the left frontal lobe, in a reference population. The second reference data VRR indicates a cumulative distribution of the second value for the corresponding portion, e.g. the right frontal lobe, in the reference population. The conversion facility 14L, 14R determines a third value VPL that indicates the cumulative probability of the first value VL according to the first reference data VRL. The conversion facility 14L, 14R further determines a fourth value VPR that indicates the cumulative probability of the second value VR according to the second reference data VRR. The output device 16 generates a human accessible output signal SH which is indicative for a substantially monotonically increasing function of a difference between the third and the fourth value VPL, VPR.

In the embodiment shown, the apparatus 10 is part of a system 50, which further comprises one or more of:

- a scanning device 52L, 52R with image analysis functionality for determining the first value VL and the second value VR; and
- a storage facility 54L, 54R for storing and providing said first and said second reference data VRL, VRR.

The apparatus is also connected to a computer accessible medium 30.

Although some elements of the system are shown as separate parts they may implemented in practice as a single part. For example the conversion facility 14L, 14R may be a single facility that applies the conversion to both the first value VL and the second value VR. Likewise, the scanning device 52L, 52R with image analysis functionality may be a single facility and the a storage facility 54L, 54R may be a single facility.

Figure 2:
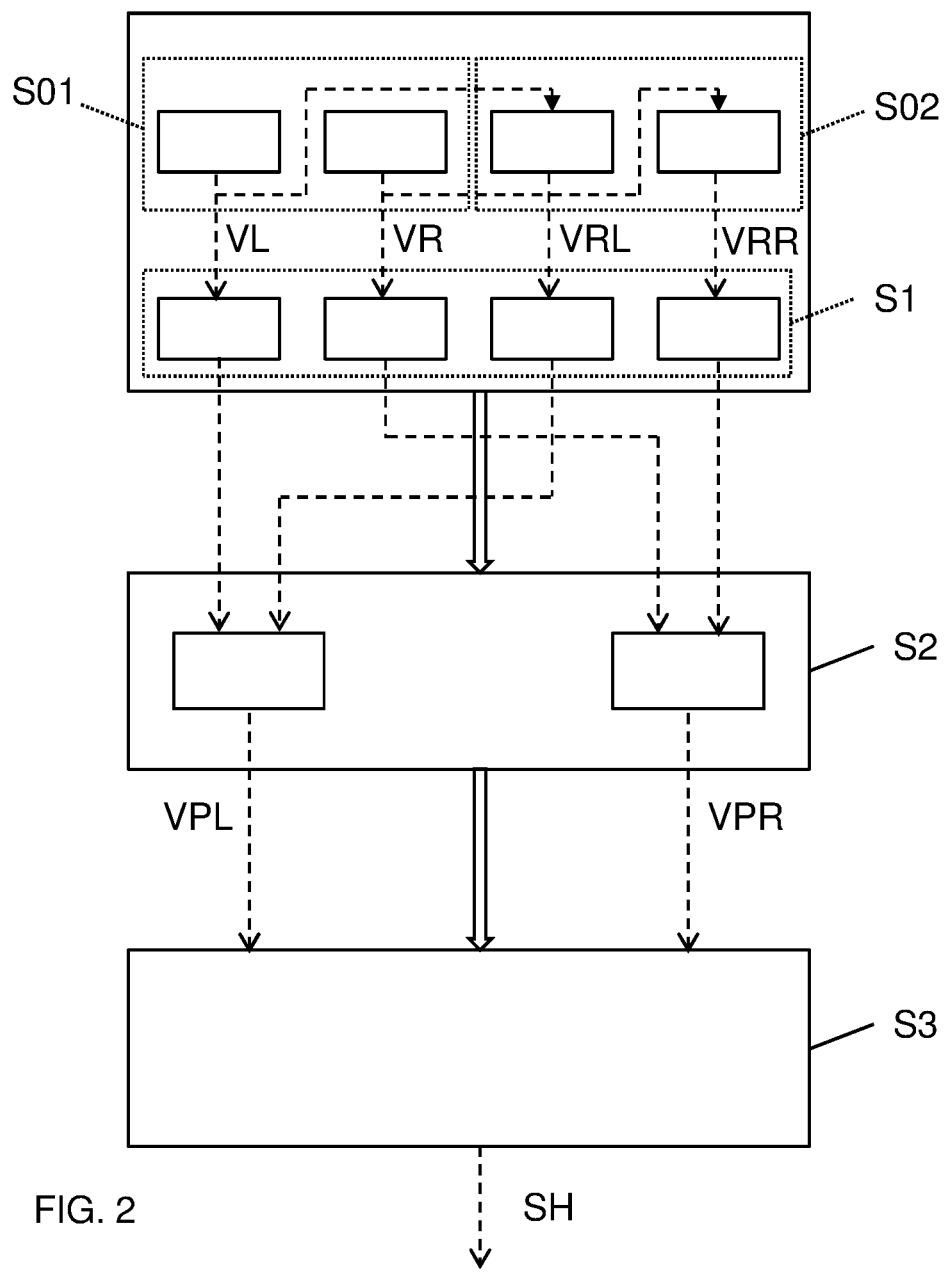

FIG. 2 schematically shows a method for assisting in providing a diagnosis of a medical condition of a mammal brain, the brain having a left and a right part.

In a first step S1 of the method of FIG. 2, at least one pair of values VL, VR as well as at least one pair of reference values VRL, VRR is received. The at least one pair of values includes a first value VL indicative of a brain characteristic of a portion of the left part of the brain for a point in time and a second value VR indicative of a brain characteristic of a corresponding portion of the right part of the brain for that point in time.

The at least one pair of reference values includes first reference data VRL indicative for a cumulative distribution of the value for said portion in a reference population and second reference VRR data indicative for a cumulative distribution of the second value for the corresponding portion in the reference population.

The method may include a step S01 of establishing the at least one pair of values VL, VR, for example using a scanning device, such as an MRI device or a CT-scanner for obtaining three dimensional image data and using image analysis tools to derive the pair of values from the obtained three dimensional image data. The three dimensional image data may be represented as pixels in a series of two-dimensional images, or as voxels in a single three dimensional image. The three dimensional image data may be stored, for example in a compressed format. Alternatively the image data may be deleted after the at least one pair of values VL, VR is derived from the image data.

Alternatively, this data may be already available on a data carrier and be retrieved in step S1 for example using a wired or wireless data-connection. Typically the reference data VRL, VRR will already be obtained is step S02 in earlier investigations and be available on a data carrier, so that it can be retrieved therefrom using a wired or wireless data-connection. Certain embodiments can be contemplated wherein the reference data is locally obtained.

For example the method could be performed by a scanning device capable to obtain three dimensional image data that is equipped with image analysis tools for generating the reference data from the three dimensional image data as input for step S02.

As indicated above, the at least one pair of reference values includes reference data indicative for a cumulative distribution of the values in a reference population. The distribution of each value for the reference population may be indicated in various ways.

According to a first approach the cumulative distribution of a value of a brain characteristic of portion of a reference population may be indicated by a set of percentile values. Therein each percentile value $P_x$ specifies that for a particular percentage of the reference population a value of said brain characteristic lower than said percentile value is determined. E.g. 50% of the reference population has a value for said brain characteristic lower than $P_{50}$ and 10% of the reference population has a value for said brain characteristic lower than $P_{10}$.

Alternatively, it may be contemplated to specify the reference distribution in other terms. For example if it is known that brain characteristic of the reference population is always distributed according to a particular type of distribution, it is sufficient to know the values of the parameters of the distribution and the percentile values can subsequently be calculated using these parameter values. For example if the reference distribution is known to be a cumulative normal distribution it is sufficient to provide a mean and a standard deviation of that normal distribution. For some type of distributions, e.g. a Poisson distribution, a single parameter is sufficient for this purpose.

In step S2 a third value VPL is determined, that indicates the cumulative probability of the first value VL according to the first reference data VRL. Also a fourth value VPR is determined, that indicates the cumulative probability of the second value VII according to said second reference data VRR. E.g. the third value VPL indicates the percentage of the reference population having a value for the brain characteristic of a portion of the brain less than the value VL. Likewise the fourth value VPR indicates the percentage of the reference population having a value for the brain characteristic of a portion of the brain less than the value VR. It will be understood that instead of percentage another, equivalent indicator can be used. E.g. instead of a percentage, a fraction can be indicated. Still alternatively, the third value or the fourth value may respectively indicate the percentage or the fraction of the reference population for which a value higher than the measured value VL or VR was found.

It is noted that the third and the fourth value VPL, VPR do not need to exactly indicate the respective fractions or percentages. For example using a set of ten percentile values $P_{10}, P_{20}, \ldots, P_{100}$, a percentage x may be selected from the corresponding values $10, 20, \ldots, 100$ as the third or the fourth value. E.g. if the value VL is less than P30, but greater than P20, the corresponding value 30 is returned as the value VPL.

Using the data obtained in the second step S2, a third step S3 is performed, wherein a human accessible output signal SH is generated that is indicative for a substantially monotonically increasing function of a difference between the third and the fourth value.

In the embodiment shown in FIG. 1, the apparatus comprises a programmable computer and a computer accessible medium 30 is provided that comprises a computer program with instructions for causing the programmable computer to execute the steps as specified. Alternatively the steps as specified may be executed by dedicated hardware, in which case it is not necessary to provide instructions. In again another embodiment some components may be provided as dedicated hardware, while other components are programmable.

Figure 3:
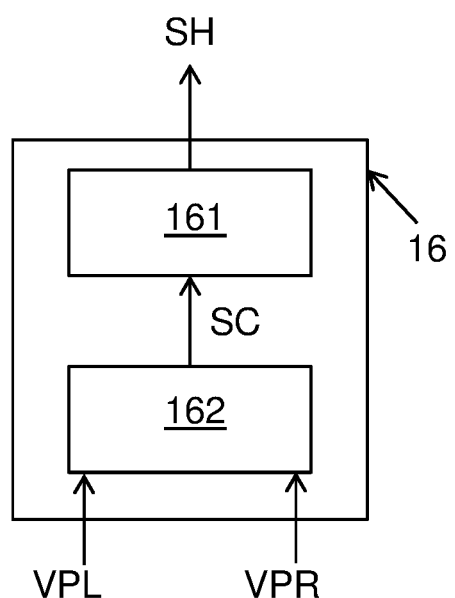
FIG. 3 shows part of an embodiment of the apparatus of FIG. 1.

FIG. 3 shows part of an embodiment of the apparatus. In the embodiment shown therein the output device 16 comprises a display unit 161 and a control unit 162 that generates control signals SC for the display unit.

Figure 4:
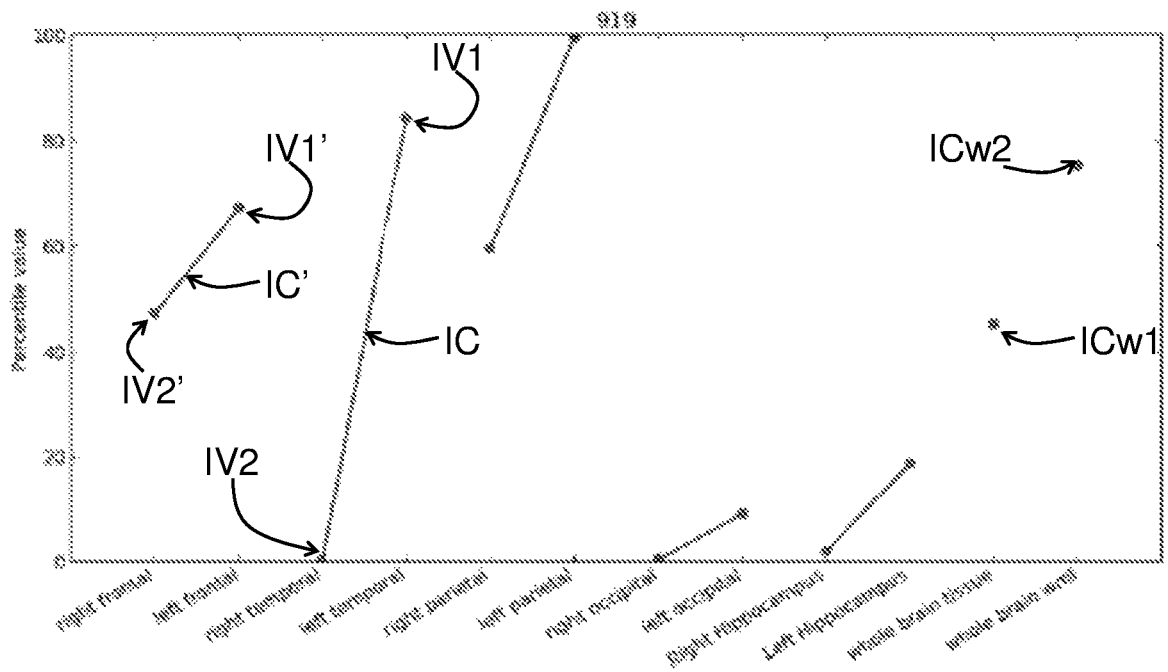
FIG. 4 illustrates an operational state of the embodiment of the apparatus of FIGS. 1 and 3.

FIG. 4 illustrates an operational state of the embodiment of the apparatus of FIGS. 1 and 3. Therein the control unit 162 (see FIG. 3) causes the display unit 161 (see FIG. 3) to display an icon IC, for example a line, having a first vertex IV1 which is determined by the third value VPL and a second vertex IV2 which is determined by the fourth value VPR.

In the embodiment of FIG. 4, the control unit 162 causes the display unit 161 to display a plurality of icons IC, IC'. In addition to the icon IC, which is associated with the left and right temporal lobes, for example a further icon IC' is displayed, which is associated with the left and right frontal lobes.

As the third value VPL indicates the cumulative probability of the first value VL in accordance with the first reference data and the fourth value VPR indicates the cumulative probability of the second value VR according to the second reference data (VRR), the icon IC has a size that is indicative for a substantially monotonically increasing function of a difference between the third and the fourth value VPL, VPR. In other words, the output device 16 therewith generates a human accessible output signal (SH) which is indicative for a substantially monotonically increasing function of a difference between the third and the fourth value VPL, VPR. This applies similarly to other icons displayed in this embodiment, e.g. the icon IC'. Therewith, the image rendered by the output device 16 provides, in a single overview, information on the extent of asymmetry for various brain characteristics in terms of their distribution known from the reference population. This can be used as objective, quantitative information to support the diagnosis of a wide range of neurological diseases as is set out in more detail below. The values VL, VR, VPL, VPR indicate a volume of a paricular brain portion. In addition FIG. 4 shows two further icons ICw1 and ICw2. ICw1 indicates the cumulative probability of a value determined for the combined volume of the grey and white matter tissue, according to reference data indicating the distribution of that value for a reference population. ICw2 indicates the cumulative probability of a value determined for the whole brain white matter lesion volume, according to reference data indicating the distribution of that value for a reference population.

In the embodiment illustrated with FIG. 4 the plurality of icons are IC, IC' are arranged in mutually distinct spatial regions. In this case the spatial regions are arranged next to each other in a horizontal direction. Accordingly, the icons can be identified by their position on the display.

Figure 4A:
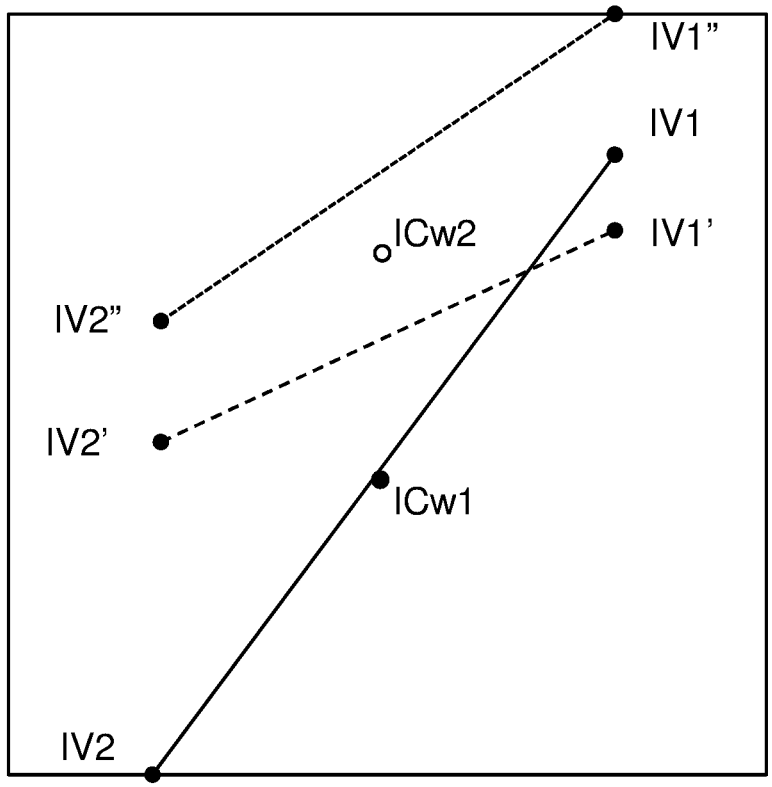
FIG. 4A illustrates an operational state of an alternative embodiment of the apparatus of FIGS. 1 and 3.

FIG. 4A illustrates an operational state of an alternative embodiment of the apparatus of FIGS. 1 and 3. In this embodiment the icons share a common spatial region. This enables an even better comparison between the various portions of the brain. In the embodiment shown the individual icons IV1, IV2, IV1', IV2', IV1", IV2", ICw1, ICw2 can be identified by their labels. By way of examples the icons IV1, IV2, IV1', IV2' and IV1", IV2" can also be recognized by their appearance, here as a solid line, a dashed line and a dotted line. Icons ICw1, ICw2 are shown as a dark dot and a light dot. Alternatively or additionally, the different icons may be displayed in mutually different colors.

Figure 5:
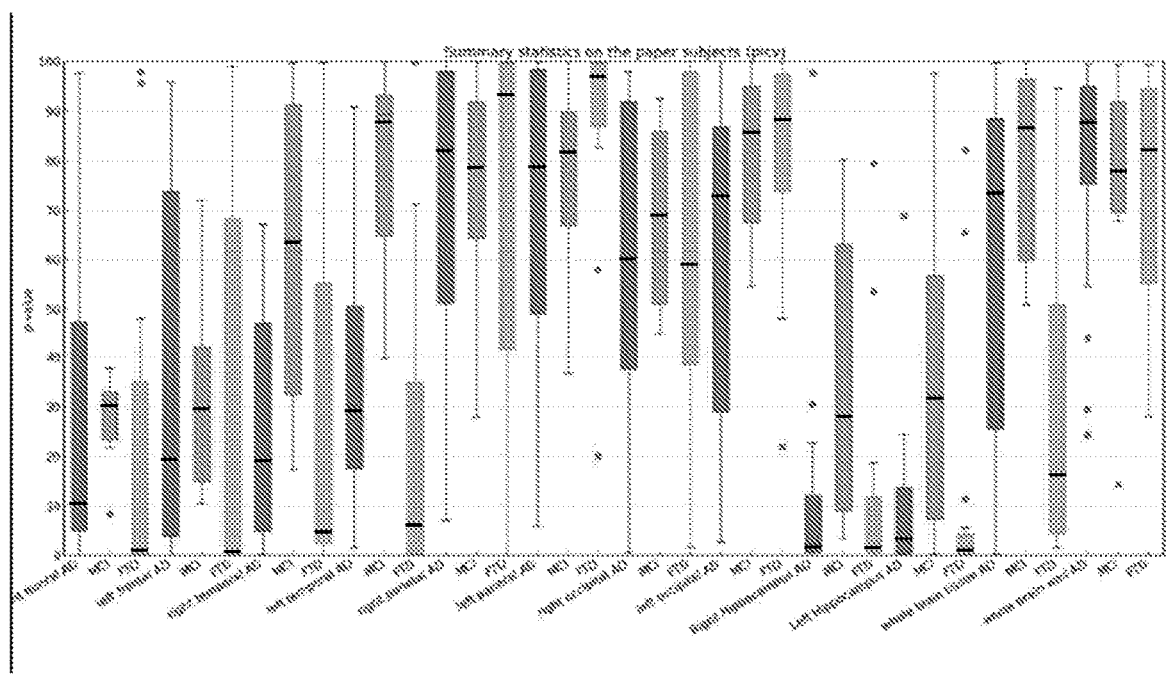
FIG. 5 shows statistic data obtained from groups of subjects having various mental impairments.

It has been found that the human accessible output signal SH obtained in this way is strongly indicative for the presences of certain mental disorders. By way of example FIG. 5 shows statistic data obtained from groups of subjects having Alzheimer disease (AD), mild cognitive impairment (MCI) and fronto-temporal dementia (FTD). The diagnosis of these subjects is based on expert consensus review of clinical, laboratory and nuclear imaging data in combination with visual inspection of brain MRI images.

Figure 9:
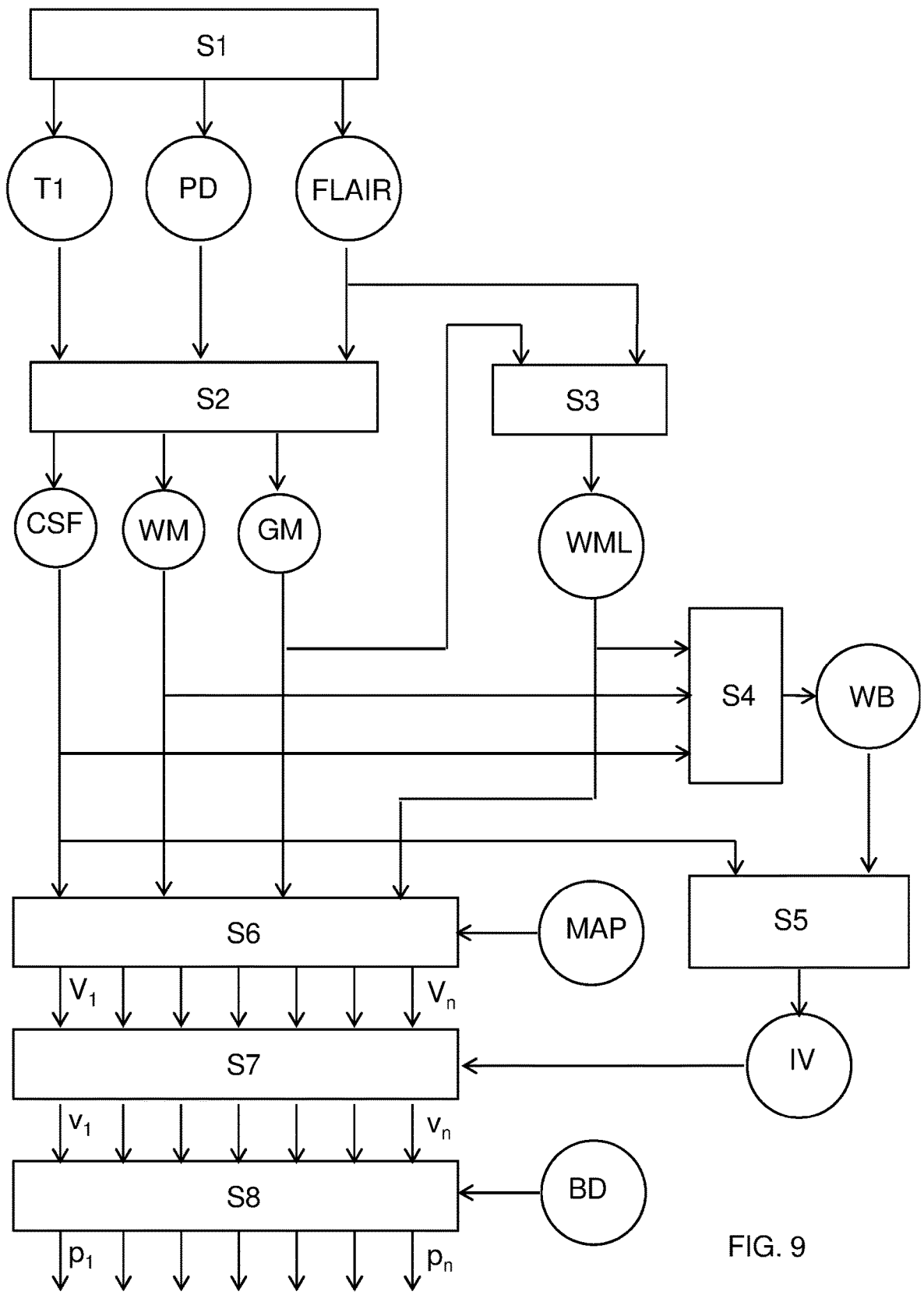
FIG. 9 illustrates in more detail an exemplary method of preparing reference data.

FIG. 9 schematically illustrates how reference data was obtained from a healthy reference group of 5000 participants who were non-demented at time of MRI, as was part of the study exclusion criteria De Leeuw et al., Neurol Neurosurg Psychiatry. 2001 January; 70(1):9-14, Ikram et al., Eur J Epidemiol. 2011 October; 26(10):811-24. Epub 2011 Oct. 16, and Hofman et al., Eur J Epidemiol. 1991 July; 7(4): 403-22.

MRI images were obtained from each of the 5000 reference subjects as shown in step S1 using a 1.5 T MRI system (General Electric Healthcare, Milwaukee, Wis.). The imaging protocol included a T1-weighted 3-dimensional fast radiofrequency spoiled gradient recalled acquisition in steady state with an inversion recovery prepulse sequence (TR=13.8 milliseconds, TE=2.8 milliseconds, inversion time=400 milliseconds, FOV=25×17.5 cm2, matrix=416× 256 [interpolated to 512×512], flip angle=20°, NEX=1, bandwidth [BW]=12.50 kHz, 96 slices with a thickness=1.6 mm zero-padded in the frequency domain to 0.8 mm, interpolated voxel size=0.5×0.5×0.8=0.2 mm3), a proton density (PD)–weighted sequence (TR=12 300 milliseconds, TE=17.3 milliseconds, FOV=25×17.5 cm2, matrix=416× 256, NEX=1, BW=17.86 kHz, 90 slices with slice thickness=1.6 mm), and a fluid-attenuated inversion recovery (FLAIR) sequence (TR=8000 milliseconds, TE=120 milliseconds, inversion time=2000 milliseconds, FOV=25×25 cm2, matrix=320×224, NEX=1, BW=31.25 kHz, 64 slices with slice thickness=2.5 mm). All slices were contiguous.

The MRI brain images of type T1, PD, and FLAIR so obtained were uploaded to a Linux workstation. Segmentation of brain tissue into gray matter (GM), white matter (WM), white matter lesions (WML) and cerebrospinal fluid (CSF) was performed using an automated algorithm as described by Cocosco et al. Med Image Anal 7 (4), 513-527 and Vrooman et at Neuroimage. 2007 Aug. 1; 37(1):71-81. Epub 2007 May 21, with an extension for WML segmentation developed by de Boer et al. Neuroimage. 2009 May 1; 45(4):1151-61.

In short, in step S2, the T1, PD and FLAIR MRI images were registered and segmented in GM, WM and CSF using an automatically trained K-nearest-neighbor (Knn) classifier. Automatic training was achieved by non-rigid registration of GM, WM and CSF probability atlases, providing subject-specific training samples for subsequent Knn-classification.

After Knn classification, the GM segmentation result was used in step S3 to perform automated thresholding on the FLAIR images to segment WML. Segmentation results were multiplied by the voxel dimensions to obtain WM, GM, WML and CSF volumes in ml for the whole brain. Whole brain volume WB was calculated in step S4 by adding WM, GM and WML volumes. Intracranial volume IV was calculated in step S5 by adding WM, GM, WML and CSF volumes.

Hippocampal volumes were determined using FreeSurfer, i.e. a brain imaging software package developed by the Athinoula A. Martinos Center for Biomedical Imaging at Massachusetts General Hospital for analyzing magnetic resonance imaging (MRI) scan data. Also other methods can be used to determine the reference data for the hippocampal volume reference data provided that the same method is used to determine hippocampal volume data of the individual to be compared with the reference data.

A brain atlas MAP was prepared by outlining brain regions on brain MRI images of 12 healthy individuals using anatomical landmarks provided by Bokde et al, Brain Res Brain Res Protoc. 2005 April; 14(3):135-45. All resulting anatomical atlases were non-rigidly registered, to the brain MRI images of the subject under investigation with the Elastix toolkit, See Klein et al. IEEE Trans Med Imaging. 2010 January; 29(1):196-205. The eventual subject-tailored anatomical atlas MAP was obtained by merging the 12 anatomical atlases, using majority voting for the definitive label of each voxel. The definitive anatomical atlas MAP was used in step S6 to mask the original segmentation results, from which volumes $V_1, \ldots V_n$, for each brain lobe were calculated. All resulting volumes were divided by intracranial IV volume in step S7, to obtain relative volumes $v_1, \ldots, v_n$ . . . .

In step S8, age- and sex specific percentile curves were generated $p_1, \ldots, p_n$ for each quantified parameter (whole brain volume, lobar brain volumes, hippocampal volumes and WML volume) from the data obtained in step and further using the bibliographical data BD of the reference subjects. Step S8 was performed with an algorithm based on the LMS method (Cole et al., 1992).

In short, the LMS method estimates the box-cox power transformation ($\lambda$), mean ($\mu$) and coefficient of variation ($\sigma$) for the appropriate volume at each value of the covariate age. From these parameters, percentile lines can be estimated for the appropriate age range.

Figure 10:
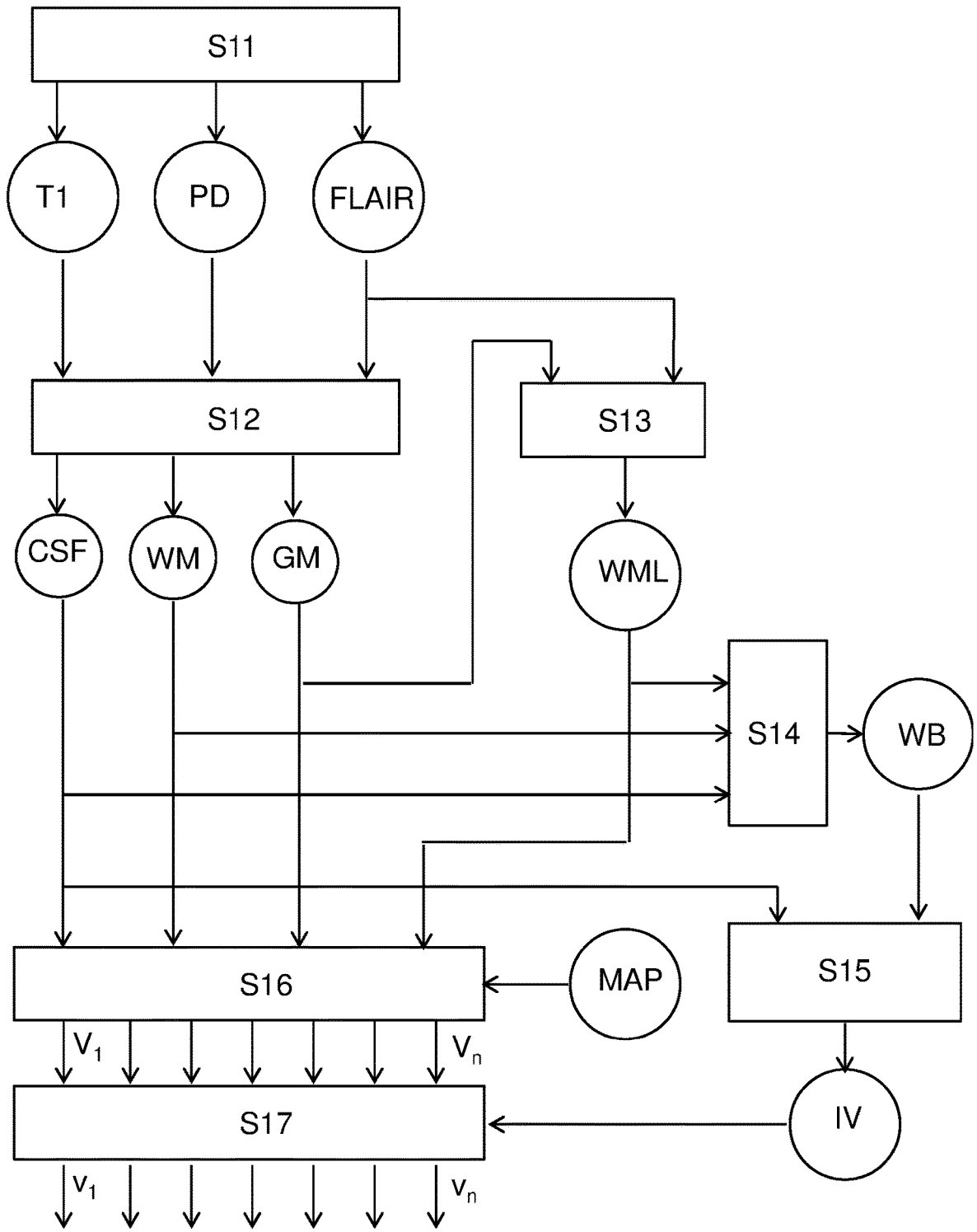
FIG. 10 illustrates in more detail a method of preparing data for use in diagnosis of an individual.

In a similar manner the relative volume data $v_1, \ldots, v_n$ is obtained from individuals to be diagnosed, as schematically indicated in FIG. 10. Therewith each step $S_k$ corresponds to a step $S_{k-10}$ in FIG. 9. I.e. steps S11 to S17 in FIG. 10 correspond to steps S1 to S7 of FIG. 9 respectively. The relative volume data $v_1, \ldots, v_n$ therewith obtained serves as the values VL, VR indicative of a brain characteristic of a brain portion of the individual for a point in time.

The percentile lines $p_1, \ldots, p_n$ so obtained in step S8 of FIG. 9 serve as the reference data VRL, VRR indicative for a cumulative distribution of the values VL, VR in a reference population.

An overview of statistical data of 42 individuals having a diagnosis of a cognitive impairment is provided in the following table. Therein the size N of each of these groups mild cognitive impairment (MCI), Alzheimer disease (AD), fronto-temporal dementia (FTD) is indicated between brackets. The table further indicates for each of these groups mean and standard deviation (SD) of the age of the subjects, the ratio between the genders, the average duration of time expired since the diagnosis. The table further indicates the values assessed by a minimal mental state examination (MMSE). The indication includes the median value as well as the interquartile range (IQR).

TABLE 1

Overview of statistical data for 42 individuals having a cognitive impairment.

|  | MCI (N = 6) | AD (N = 21) | FTD (N = 15) | Total (N = 42) |
|---|---|---|---|---|
| Age |  |  |  |  |
| Mean (SD) | 63.2 (8.5) | 66.1 (8.5) | 60.0 (6.5) | 63.5 (8.1) |
| Gender |  |  |  |  |
| M;F | 2:4 | 12:9 | 9:6 | 23:19 |
| Duration (yrs) |  |  |  |  |
| mean (SD) | 1.1 (1.8-3.6) | 2.1 (1.1-3.3) | 2.1 (1.5-3.0) | 2.1 (1.3-3.2) |
| MMSE |  |  |  |  |
| median, IQR | 25.5 (23.0-26.8) | 24.0 (22.0-25.0) | 25.5 (22.5-29.0) | 24.5 (22.3-27.0) |

FIG. 5 shows for each of these groups of subjects how the brain characteristic value for a particular portion of the left brain hemisphere is distributed in comparison to the reference distribution for that value for the same particular portion of the left brain hemisphere obtained from the healthy reference group of 5000 participants.

Likewise this comparison is shown for the brain characteristic value for the corresponding particular portion of the right brain hemisphere. The particular portions considered in this case are the mutually corresponding left and right frontal lobe, left and right temporal lobe, left and right parietal lobe, left and right occipital lobe, and the left and right hippocampus. In addition the comparison is made for "whole brain tissue" (grey and white matter volume) and the whole brain white matter lesion volume. In FIG. 5, the lower and upper boundary of the boxes respectively indicates the percentiles 25 and 75. The whiskers indicate the percentiles corresponding to 1.5 times the interquartile range (IQR).

By way of example it can be seen that the data obtained for group AD for the right frontal lobe the median value corresponds to $P_{10}$ of the reference distribution. Furthermore the range of values between $P_{25}$ and $P_{75}$ of the distribution obtained for this group corresponds to the range $P_{05}$ to $P_{47}$ of the reference group.

Returning now to the example of FIG. 4, it will be appreciated that the human accessible output signal SH as being provided therein shows a remarkable asymmetry. In particular the vertex IV1 of the signal SH indicates that the third value VPL=85, indicating the cumulative probability of the first value according to the first reference data is relatively high. Contrary thereto, the vertex IV2 of the signal SH indicates that the fourth value VPR=0 for the cumulative probability of the second value according to the second reference data is relatively low for the temporal lobes.

The medical specialist would tend to consider the diagnosis frontal temporal dementia as a possible explanation for this particular signal SH. This possible diagnosis is further supported by the observation pertaining to the frontal lobes. For the left frontal lobe, the vertex IV1' of the signal SH indicates that the third value VPL=70, i.e. the cumulative probability of the first value according to the first reference data is relatively high. Contrary thereto, for the right frontal lobe the vertex IV2' of the signal SH indicates that the fourth value VPR=0 i.e. the cumulative probability of the second value according to the second reference data is relatively low.

Figure 6:
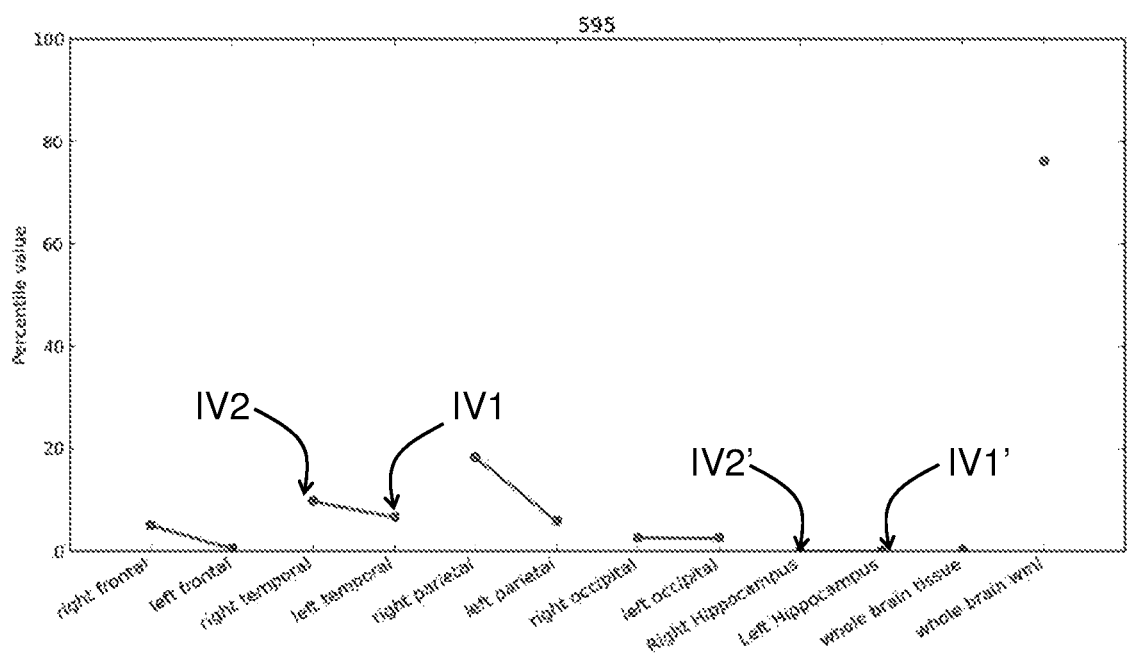
FIG. 6 illustrates another operational state of the embodiment of the apparatus of FIGS. 1 and 3.

As another example, FIG. 6 shows the human accessible output signal SH as generated by the present method for another person. In this case the vertices IV1, IV2 of the human accessible output signal SH for the temporal lobes show that the third value VPL and the fourth value VPR both are very low, i.e. about 5% and 10% respectively. I.e. a substantial atrophy as compared with the reference population is indicated for both temporal lobes.

The same is determined for each of the other parts of the brain. In particular human accessible output signal SH' indicates by vertices IV1', IV2', that also a substantial symmetric atrophy occurred, in the hippocampi. Also a symmetric atrophy in the parietal lobes would support this diagnosis, in particular for younger Alzheimer patients. By taking into account the age of the reference population in generating the first and second reference data a more reliable diagnosis can be given. On the one hand avoiding that normal atrophy occurring with elderly erroneously results in the diagnosis of Alzheimer. On the other hand it is avoided that a certain degree of atrophy which as such be normal for an older person would not be recognized as a indication of Alzheimer when diagnosing a younger person.

Figure 8:
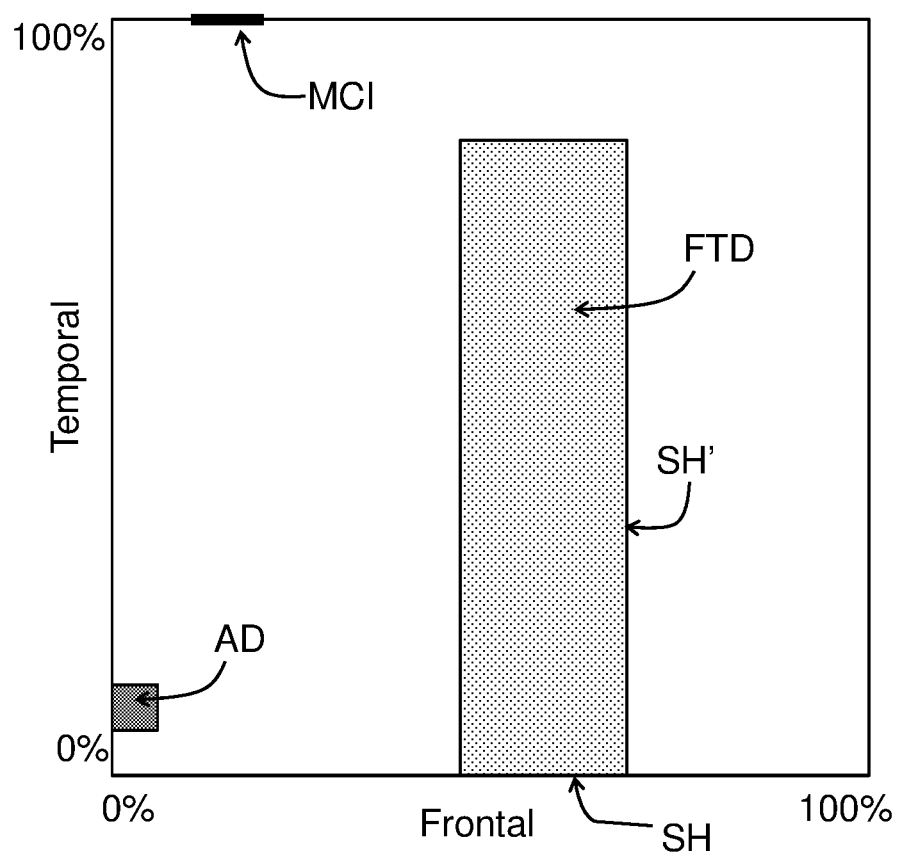
FIG. 8 illustrates an operational state of another embodiment of the apparatus of FIGS. 1 and 3.

As a further example, FIG. 8 shows the human accessible output signal SH as generated by the present method for again another person. It will be appreciated in the example shown that the human accessible output signal SH indicates that both the third value VPL and the fourth value VPR as determined for the temporal lobes is extremely high, i.e. about 100%. This provides an indication for an impairment other than Alzheimer or fronto-temporal dementia. The medical specialist may in that connection consider the diagnosis MCI as this is an further important class of mental disorders occurring with the elderly. To verify this, the medical specialist may observe further human accessible output signals, such as a signal indicating a substantially monotonically increasing function of a difference between the third and the fourth value for the frontal lobes. In that case the medical specialist observes that the third and the fourth values the frontal lobes are very low i.e. 10% and 25% as compared to the reference group. In view of the low value indicated for both sides the suspicion that the person suffers from Mild Cognitive Impairment is reinforced.

FIG. 8 shows operation of a further embodiment. In particular, in the embodiment shown, the output device generates a first and a second human accessible output signal which each are indicative for a substantially monotonically increasing function of a difference between a third and a fourth value. In particular the output device generates the first and the second human accessible output signal for the frontal lobes and the temporal lobes respectively.

To that end the output device generates an image of a rectangle. Its horizontal side extends over a trajectory determined by the third value VPL and the fourth value VPR for the frontal lobes. More in particular the horizontal side extends from a first coordinate indicating the lowest one to a second coordinate indicating the highest one of this third value VPL and this fourth value VPR. The vertical side of the rectangle extends over a trajectory determined by the third value VPL and the fourth value VPR for the temporal lobes. More in particular the vertical side extends from a first coordinate indicating the lowest one to a second coordinate indicating the highest one of this third value VPL and this fourth value VPR.

It will be understood that during normal operation, the output device 16 only shows a human accessible output signals SH, SH' as determined for a particular person for which a diagnosis has to be made. For illustrative purposes, FIG. 8 shows the human accessible output signals SH, SH' that would be generated by the apparatus for each of the three cases presented with reference to FIGS. 4, 6 and 7 respectively. From this combined view it is immediately clear that the rectangle that is rendered by the output device 16 based on the combination of human accessible output signals SH, SH' is strongly indicative for the type of mental disorder.

Particularly notifiable is the rectangle denoted as FTD, which is rendered on the basis of the same data as used for FIG. 4. In this case the first human accessible output signal SH indicates a substantial difference between the third and the fourth value for the frontal lobes. The second human accessible output signal SH' indicates a substantial difference between the third and the fourth value for the temporal lobes. Therewith the generally asymmetric nature of the atrophy occurring with fronto temporal dementia is clearly visualized by the output device 16 as a rectangle having a large area.

As a further example, the rectangle denoted as AD, is shown, which is rendered on the basis of the same data as used for FIG. 6. In this case the first human accessible output signal SH indicates that the third and the fourth value for the frontal lobes are both extremely low. The second human accessible output signal SH' indicates further that the third and the fourth value for the temporal lobes are extremely low. Therewith the generally symmetric nature of the atrophy occurring with Alzheimer disease in multiple parts of the brain is clearly visualized by the output device 16 as a small rectangle in the lower left part of the image.

Figure 7:
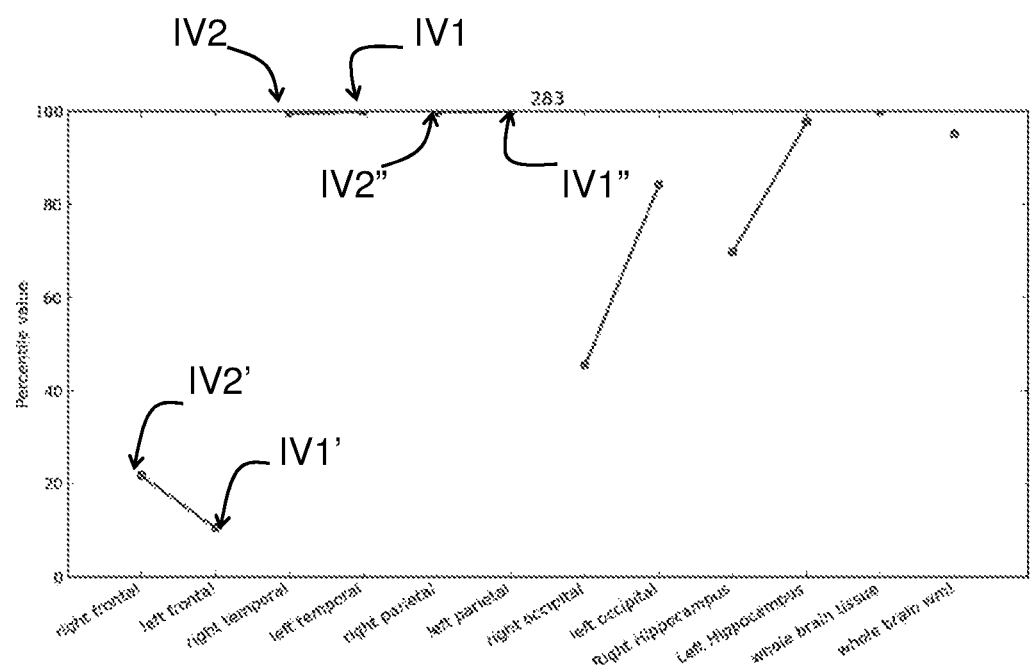
FIG. 7 illustrates again another operational state of the embodiment of the apparatus of FIGS. 1 and 3.

As a still further example, the rectangle denoted as MCI, is shown, which is rendered on the basis of the same data as used for FIG. 7. In this case the first human accessible output signal SH indicates that the third and the fourth value for the frontal lobes are both extremely low. Contrary thereto, the second human accessible output signal SH' indicates that the third and the fourth value for the temporal lobes are extremely high. Therewith the generally symmetric nature of the atrophy occurring with mild cognitive impairment in selected parts of the brain is clearly visualized by the output device 16 as a small rectangle in the upper left part of the image.

LIST OF CITED DOCUMENTS

[1] de Boer R, Vrooman H A, Ikram M A, Vernooij M W, Breteler M M B, van der Lugt A, Niessen W J. Accuracy and reproducibility study of automatic MRI brain tissue segmentation methods. NeuroImage. 2010; 51(3):1047-56.
[2] Vrooman H A, Cocosco C A, van der Lijn F, Stokking R, Ikram M A, Vernooij M W, Breteler M M B, Niessen W J. Multi-spectral brain tissue segmentation using automatically trained k-Nearest-Neighbor classification. NeuroImage. 2007; 37(1):71-81.
[3] de Boer R, Vrooman H A, van der Lijn F, Vernooij M W, Ikram M A, van der Lugt A, Breteler M M B, Niessen W J. White matter lesion extension to automatic brain tissue segmentation on MRI. NeuroImage. 2009; 45(4):1151-61.
[4] Van der Lijn F, Verhaaren B F J, Ikram M A, Klein S, De Bruijne M, Vrooman H A, Vernooij M W, Hammers A, Rueckert D, Van der Lugt A, Breteler M M B, Niessen W J. Automated measurement of local white matter lesion volume. NeuroImage. 2012; 59(4):3901-8.
[5] Van Der Lijn F, De Bruijne M, Klein S, Den Heijer T, Hoogendam Y Y, Van Der Lugt A, Breteler M M B, Niessen W J. Automated brain structure segmentation based on atlas registration and appearance models. IEEE Transactions on Medical Imaging. 2012; 31(2):276-86.
[6] van der Lijn F, den Heijer T, Breteler M M B, Niessen W J. Hippocampus segmentation in M R images using atlas registration, voxel classification, and graph cuts. NeuroImage. 2008; 43(4):708-20.
[7] Achterberg H C, van der Lijn F, den Heijer T, Vernooij M W, Ikram M A, Niessen W J, de Bruijne M. Hippocampal shape is predictive for the development of dementia in a normal, elderly population. Human Brain Mapping. 2014; 35(5):2359-71.
[8] de Groot M, Ikram M A, Akoudad S, Krestin G P, Hofman A, van der Lugt A, et al. Tract-specific white matter degeneration in aging. The Rotterdam Study. Alzheimer's and Dementia. 2014.
[9] De Groot M, Vernooij M W, Klein S, Ikram M A, Vos F M, Smith S M, Niessen W J, Andersson J L R. Improving alignment in Tract-based spatial statistics: Evaluation and optimization of image registration. NeuroImage. 2013; 76:400-11.
[10] de Boer R, Schaap M, van der Lijn F, Vrooman H A, de Groot M, van der Lugt A, Ikram M A, Vernooij M W, Breteler M M B, Niessen W J. Statistical analysis of minimum cost path based structural brain connectivity. NeuroImage. 2011; 55(2):557-65.
[11] Bron E E, Steketee R M, Houston G C, Oliver R A, Achterberg H C, Loog M, van Swieten J C, Hammers A, Niessen W J, Smits M, Klein S. Diagnostic classification of arterial spin labeling and structural MRI in presenile early stage dementia. Human Brain Mapping. 2014.

The invention claimed is:

1. An apparatus for assisting in providing a diagnosis of a medical condition of a mammal brain, the brain having a first and a second part, the apparatus including an input facility, a conversion facility, and an output device comprising a display unit for generating an output signal, the apparatus being configured and arranged such that in an operational mode of the apparatus the input facility receives from a scanning device with image analysis functionality at least one pair of values and receives from a storage facility at least one pair of reference values, the at least one pair of values including:
 a first value indicative of a brain characteristic of a portion of the first part of the brain for a point in time;
 a second value indicative of a brain characteristic of a corresponding portion of the second part of the brain for said point in time;
the at least one pair of reference values including:
 first reference data indicative for a cumulative distribution of said first value for said portion in a reference population; and
 second reference data indicative for a cumulative distribution of said second value for said corresponding portion in said reference population;
wherein the conversion facility determines a third value, indicating the cumulative probability of said first value according to said first reference data and a fourth value, indicating the cumulative probability of said second value according to said second reference data, and wherein the display unit generates as the output signal an output signal that is indicative for a monotonically increasing function of a difference between the third and the fourth value.

2. The apparatus according to claim 1, wherein the first part is the left hemisphere of the brain and the second part is the right hemisphere of the brain.

3. The apparatus according to claim 1, wherein the output device comprises the display unit and a control unit for said display unit.

4. The apparatus according to claim 3, wherein in an operational state of the apparatus said control unit causes said display unit to display an icon having a first vertex which is determined by the third value and a second vertex which is determined by the fourth value.

5. The apparatus according to claim 4, wherein in the operational state of the apparatus said control unit causes said display unit to display a plurality of icons having a respective pair of the first vertex and the second vertex, each respective pair of vertices of each icon being associated with a respective portion of the first part of the brain and its corresponding portion of the second part of the brain, the first vertex being determined by the third value for said portion and the second vertex being determined by the fourth value for said corresponding portion.

6. The apparatus according to claim 4, wherein in the operational state of the apparatus said control unit causes said display unit to display a rectangle, with first sides and second sides transverse to said first sides, which first sides extend over a trajectory determined by the third value determined by a first portion of the first part of the brain and the fourth value determined for the portion corresponding to said first portion in the second part of the brain, which second sides extend over a trajectory determined by the third value determined by a second portion of the first part of the brain and the fourth value determined for the portion corresponding to said second portion in the second part of the brain.

7. The apparatus according to claim 6, wherein a horizontal side extends from a first coordinate to a second coordinate, the first and the second coordinate respectively indicating the lowest one and the highest one of the third value for said first portion and the fourth value for said portion corresponding to the first portion, and wherein a vertical side extends from a third coordinate to a fourth coordinate, the third and the fourth coordinate respectively indicating the lowest one and the highest one of the third value for said second portion and the fourth value for said portion corresponding to the second portion.

8. The apparatus according to claim 3, wherein in an operational state of the apparatus said control unit causes said display unit to display a virtual image of the mammal brain and indicating therein said portion with a color and/or brightness as determined by said third value and said corresponding portion with a color and/or brightness as determined by said fourth value.

9. The apparatus according to claim 1, wherein in an operational state of the apparatus the at least one pair of values is obtained from at least a first and a second pair of the first value and second value, the first and the second pair of values being obtained at mutually different points in time, wherein the conversion facility determines for each of said mutually different points in time a pair of the third value and the fourth value associated with the first and the second pair of values obtained for said mutually different points in time, and wherein the output device generates a first human accessible output signal which is indicative for a monotonically increasing function of a difference between the third and the fourth value of said at least a first pair of the third and the fourth value and a second human accessible output signal which is indicative for a monotonically increasing function of a difference between the third and the fourth value of said at least a second pair of the third and the fourth value.

10. The apparatus according to claim 9, wherein the output device simultaneously generates the first human accessible output signal and the second human accessible output signal.

11. The apparatus according to claim 9, wherein the output device sequentially generates the first human accessible output signal and the second human accessible output signal in an order corresponding to the order in time in which the first and the second pair of the first value and second value were obtained and separated by a time interval that is smaller than the time interval between said mutually different points in time.

12. A system comprising an apparatus according to claim 1, and further comprising one or more of:
   the scanning device equipped with image analysis tools for determining the first value and the second value; and
   the storage facility for storing and providing said first and said second reference data.

13. A method for assisting in providing a diagnosis of a medical condition of a mammal brain, the brain having a first and a second part, the method including receiving from a scanning device with image analysis functionality at least one pair of values and receiving from a storage facility at least one pair of reference values, the at least one pair of values including:
   a first value indicative of a brain characteristic of a portion of the first part of the brain for a point in time;
   a second value indicative of a brain characteristic of a corresponding portion of the second part of the brain for said point in time;
the at least one pair of reference values including:
   first reference data indicative for a cumulative distribution of said first value for said portion in a reference population; and
   second reference data indicative for a cumulative distribution of said second value for said corresponding portion in said reference population;
   determining a third value, indicating the cumulative probability of said first value according to said first reference data and a fourth value, indicating the cumulative probability of said second value according to said second reference data, and
   displaying an output signal which is indicative for a monotonically increasing function of a difference between the third and the fourth value.

14. A non-transitory computer accessible medium comprising a computer program with instructions for causing a programmable computer to execute a method for assisting in providing a diagnosis of a medical condition of a mammal brain, the brain having a first and a second part, the method including
   receiving from a scanning device with image analysis functionality at least one pair of values and receiving from a storage facility at least one pair of reference values, the at least one pair of values including:
   a first value indicative of a brain characteristic of a portion of the first part of the brain for a point in time;
   a second value indicative of a brain characteristic of a corresponding portion of the second part of the brain for said point in time;
   the at least one pair of reference values including:
   first reference data indicative for a cumulative distribution of said first value for said portion in a reference population; and
   second reference data indicative for a cumulative distribution of said second value for said corresponding portion in said reference population;
   determining a third value, indication the cumulative probability of said first value according to said first reference data and a fourth value, indicating the cumulative probability of said second value according to said second reference data, and
   displaying an output signal which is indicative for a monotonically increasing function of a difference between the third and the fourth value.

* * * * *